United States Patent [19]

Allain et al.

[11] 4,306,983

[45] Dec. 22, 1981

[54] PROCESS FOR PREPARING OVERBASED MAGNESIUM SULFONATES

[75] Inventors: Ronald J. Allain; Dodd W. Fong, both of Richmond, Tex.

[73] Assignee: Nalco Chemical Company, Oak Brook, Ill.

[21] Appl. No.: 184,156

[22] Filed: Sep. 4, 1980

Related U.S. Application Data

[63] Continuation of Ser. No. 24,230, Mar. 26, 1979, abandoned.

[51] Int. Cl.$^3$ .............................................. C10M 1/40
[52] U.S. Cl. .................................... 252/33.3; 252/18; 252/25; 252/33; 252/33.2; 252/33.4
[58] Field of Search .................... 252/18, 25, 33, 33.2, 252/33.3, 33.4

[56] References Cited

U.S. PATENT DOCUMENTS

| | | | |
|---|---|---|---|
| 3,223,630 | 12/1965 | Gragson | 252/18 X |
| 3,372,118 | 3/1968 | Rense | 252/33.4 X |
| 3,451,931 | 6/1969 | Kahn et al. | 252/25 X |
| 3,539,511 | 11/1970 | Sabol et al. | 252/33.4 X |
| 3,783,131 | 1/1974 | LeSuer | 252/25 X |
| 3,857,790 | 12/1974 | Saunders et al. | 252/18 X |
| 4,049,560 | 9/1977 | Dominey | 252/25 X |
| 4,059,536 | 1/1977 | Lallement et al. | 252/25 X |

*Primary Examiner*—Arthur P. Demers

*Attorney, Agent, or Firm*—John G. Premo; Robert A. Miller; John S. Roberts, Jr.

[57] ABSTRACT

A method of preparing overbased or superbased magnesium sulfonates by sulfonating an alkyl benzene with a material containing $SO_3$, preferably oleum, and reacting the alkyl benzene sulfonate with magnesium oxide in the presence of a low viscosity diluent, such as No. 2 oil or LOPS (low odor paraffin solvent), together with water, alcohol, and $CO_2$. The newness of the method lies in the steps of preferably positively utilizing oleum which contains a minor amount of sulfuric acid as a promoter and utilizing also a surfactant couple of a $C_{12}$-$C_{18}$ fatty acid such as oleic acid and an ethanol amide such as a lauryl diethanol amide, which may be Witcamide 5138; where a ready made sulfonate is used, such as SA697 (Conoco), $H_2SO_4$ is utilized. In certain instances the amide may be omitted with satisfactory results occurring by using the acid alone.

Of particular interest is the preparation of a concentrated magnesium sulfonate wherein the water and alcohol are removed by distillation and a diluent such as LOPS or No. 2 oil is added to produce a slurry.

An important feature of this process lies in the reduction in size of the magnesium oxide particles. $CO_2$ is preferentially bubbled through the mixture after introduction of the magnesium oxide and at a temperature range of 30°–80° C. with stirring.

8 Claims, No Drawings

PROCESS FOR PREPARING OVERBASED MAGNESIUM SULFONATES

This is a continuation of application Ser. No. 24,230, filed Mar. 26, 1979, now abandoned.

This invention relates to a method of preparing overbased or superbased magnesium sulfonates by sulfonating an alkyl benzene with a material containing $SO_3$, preferably oleum, and reacting the alkyl sulfonate with magnesium oxide in the presence of a low viscosity diluent, such as No. 2 oil or LOPS (low odor paraffin solvent), together with water, alcohol, and $CO_2$. The newness of the method lies in the steps of preferably positively utilizing oleum which contains a minor amount of sulfuric acid as a promoter or a ready made sulfonate with added sulfuric acid and utilizing also a surfactant couple of a $C_{12}$–$C_{18}$ fatty acid, such as oleic acid, and an ethanol amide, such as a lauryl diethanol amide which is Witcamide 5138. Selected surfactants suitable for practicing this invention include the following, which are particular alkanol amides produced by Witco Chemical Corporation, New York: Witcamide 272, 511, 1017, 5130, 5133, 5140, 5145M, 5168, 5195, and AL69-8. In certain instances the amide may be omitted with satisfactory results occurring by using the acid alone.

Particularly, in the method of preparing over-based magnesium sulfonates by sulfonating an alkyl benzene with a material containing $SO_3$, which material is selected from one member of the group consisting of $SO_3$ and oleum and reacting the alkyl sulfonate product with magnesium oxide in the presence of a low viscosity diluent, water, alcohol, and $CO_2$, which comprises positively utilizing oleum in the sulfonation step and additionally adding to the magnesium oxide a surfactant couple comprising a $C_{12}$–$C_{18}$ fatty acid and an alkanol amide, and in this method wherein an alkyl benzene sulfonic acid with added sulfuric acid is utilized instead of the alkyl benzene sulfonic acid, and which consists of using as the surfactant couple oleic acid and lauryl diethanol amide.

Of particular interest is the preparation of a concentrated magnesium sulfonate wherein the water and alcohol are removed by distillation and a diluent, such as LOPS or No. 2 oil, is added to produce a slurry.

An important feature of this process lies in the reduction in size of the magnesium oxide particles. $CO_2$ is preferentially bubbled through the mixture after introduction of the magnesium oxide and at a temperature range of 30°–80° C. with stirring.

In discussing size, the starting material of magnesium oxide, for example Martin Marietta's MM469, is in the range of 4–5 microns. This starting material contains about 9–11% soluble material, which is a colloidal material of about 200 Å units. The remainder of the 90% of the magnesium oxides added after the initial formation of the magnesium sulfonate in the second step is less than 1 micron or in the range actually of about 0.1–1.0 micron.

The process comprises the following steps: (1) mixing the low-viscosity diluent oil with oil-soluble alkyl benzene sulfonic acid, water, alcohol, amine and an acid, and suspending agents together; (2) charging low density MgO into step (1); (3) treating the reaction mixture with $CO_2$ at 30°–80° C. with adequate stirring; and (4) heating the final mixture to 120° C. to remove water and alcohol.

PRIOR ART STATEMENT

Of particular interest are the following U.S. Pat. Nos.:
2,695,910;
2,856,361;
3,429,811;
3,928,216;
4,129,589.

The patented art above is illustrative of many U.S. patents which have appeared in the past two decades on the present subject. In particular, in U.S. Pat. No. 3,928,216 Example 2 was used as a starting point for the present development. With reference to the recipe which is furnished in the examples and its components, the following is deemed of interest.

THE SULFONATING AGENT $SO_3$ gas or oleum have each been utilized in the past. In the event that a sulfonic acid is utilized, the following may be used: SA697 (Conoco), CHB (Witco Chemical), Dowfax 2AD (Dow Chemical). Additionally, when using alkyl benzenes, Exxon's ECA 5422 and Conoco's LMR-5 may be used. It is important to utilize sulfonic acids with a molecular weight in the range of 350–750 and especially between 400–600.

THE DILUENT OIL

The low boiling diluent oil used may well be selected from No. 2 fuel oil, for which see *Chemical Engineer's Handbook*, 5th edition, McGraw Hill, 1973, page 9–9, or LOPS (low odor paraffinic solvent), both of which have a low boiling point.

THE SURFACTANT COUPLE

The couple is defined to produce a surfactant which is a mixture of an acid and an amide. In order to accomplish this, a coupled arrangement of a fatty acid, such as oleic, is utilized, together with an alkanol amide.

THE CONCENTRATE

The product is a concentrate made by elimination of water and alcohol at up to 120° C. and replacement in part by low boiling solvents, addition of further magnesium oxide and $CO_2$ to produce a product of increased amount of magnesium which it was noted had a smaller particle size and thus was more susceptible to slurrying. The reduced particle size of the magnesium may have been due in part to the presence of the surfactant couple and other factors.

EXAMPLE 1-A

| Part I | |
|---|---|
| Sulfonic acid | 47.6 grams |
| Concentrated sulfuric acid | 5.2 grams |
| LOPS | 78.0 grams |
| Methanol | 27.3 grams |
| Part II | |
| Formic acid | 4.0 grams |
| Ethylene diamine | 2.5 grams |
| Deionized water | 36.0 grams |

Part I and Part II were mixed together and to this was added magnesium oxide, 80 grams. Additionally, $CO_2$ was charged at 0.96 liter/min. for one hour.

After one hour the water and methanol was stripped off by heating at about 120° C. The LOPS remained in the kettle having a boiling range of 188°–246° C.+. At this point 2.5 grams of toluene and 5 grams of Witcamide 5138 (lauryl diethanol amide) plus 10 grams of oleic acid were added to the pot with stirring. Finally, 60 grams of magnesium oxide was added with stirring for one hour.

EXAMPLE 1-B

A mixture of 75% LOPS and 25% high boiling aromatic solvent were substituted for the LOPS in Example 1-A above. Additionally, the Witcamide was omitted and for the surfactant only oleic acid (10 grams) plus high boiling aromatic solvent (10 grams) were utilized.

EXAMPLE 2-A

| | |
|---|---|
| LMR-5 SA (Conoco, sulfonated alkyl benzene, m.w. 385) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 2.5 grams |
| Water | 27.8 grams |
| Magnesium oxide (Martin Marietta 469) | 60.0 grams |

The above mix was heated at 35° C. with input of $CO_2$ at 0.96 liters/min. for one hour. The product had total base number (TBN) of 503. This was diluted with toluene and then was filtered to fill an extra need for a very pure product. This product had a TBN of 444.

EXAMPLE 2-B

| | |
|---|---|
| Conoco SA697 (low m.w. about 400 sulfonic acid) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 2.5 grams |
| Water | 27.8 grams |
| Magnesium oxide (Martin Marietta 469) | 60 grams |

The above mixture was heated at 45° C. with input of $CO_2$ at 0.96 liters/min. for one hour and solidified.

EXAMPLE 3-A

| | |
|---|---|
| A sulfonic acid from Exxon's ECA-5422 SA (alkyl benzene) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 2.5 grams |
| Water | 27.8 grams |
| Magnesium oxide (Martin Marietta 469) | 70.0 grams |

The above recipe was warmed at 40° C. for one hour during which time $CO_2$ at 0.96 liters/min. was bubbled in. The temperature was then raised to greater than 100° C. to remove water and methyl alcohol. The product which was quite useful unfiltered had a TBN of 549 and for special purposes when filtered had a TBN of 419.

EXAMPLE 3-B

| | |
|---|---|
| Sulfonic acid from Conoco's LMR-5 (alkyl benzene) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 25.0 grams |
| Water | 27.8 grams |
| Magnesium oxide (Martin Marietta 469) | 70.0 grams |

The above recipe was warmed at 40° C. for one hour during which time $CO_2$ was bubbled through at 0.96 liters/min. Toluene was also added and the condenser was removed and the temperature was raised to greater than 100° C. The product which was quite useful unfiltered and resistant to filtering had a TBN of 502 equivalent to 10.8% Mg.

EXAMPLE 4-A

| | |
|---|---|
| Exxon's ECA-5422 SA (alkyl benzene) sulfonated with $SO_3$ with 84% sulfonation | 46.8 grams |
| Water | 5.2 grams |
| No. 2 fuel oil | 78.0 grams |
| Oleic acid | 10.0 grams |
| Witcamide 5138 (lauryl diethanol amide) | 5.0 grams |
| Methyl alcohol | 27.3 grams |
| Formic acid | 4.0 grams |
| Ethylene diamine (EDA) | 2.5 grams |
| Water | 36.0 grams |
| Magnesium oxide (Martin Marietta 469) | 80.0 grams |

The recipe above was warmed from 48° C. to 65° C. together with bubbling $CO_2$ through at 0.96 liters/min. When the $CO_2$ sparging had ceased, the mixture was heated to about 115° C. for ½ hour to produce a viscous product with a TBN of 676, equivalent to 14.8% Mg.

EXAMPLE 4-B

| | |
|---|---|
| Alkyl benzene from Exxon's ECA 5422 sulfonated with $SO_3$ with 92% sulfonation | 46.8 grams |
| Remaining ingredients same as Example 4-A above | |

This recipe is similar to Example 4-A and in the heating procedure the heating was carried out for one hour at 45° C. gradually warming to 53° C. and concomitant with $CO_2$ charging at 0.96 liters/min. When the $CO_2$ sparging stopped, heating was increased to 115° C. for an additional ½ hour and cooled. TBN of the product was 703 equivalent to 15.2% Mg.

EXAMPLE 5

| | |
|---|---|
| Sulfonated alkyl benzene | 47.6 grams |
| Concentrated $H_2SO_4$ | 5.2 grams |
| LOPS | 78.0 grams |
| Methyl alcohol | 27.3 grams |
| Formic acid (promoter) | 4.0 grams |
| Ethylene diamine (promoter) | 2.5 grams |
| Water | 36.0 grams |
| Magnesium oxide (Martin Marietta 469) | 80.0 grams |

The above mixture was warmed at 60° C. during which time $CO_2$ at 0.96 liters/min. was bubbled through for one hour and then heated to 115° C. Then the following was added:

| | |
|---|---|
| Witcamide 5138 (lauryl diethanol amide) | 5.0 grams |
| Oleic acid | 10.0 grams |
| Magnesium oxide (Martin Marietta 469) | 60.0 grams |
| Toluene | 100.0 grams |

The above was then stirred for 10 minutes, transferred to a flask, stripped of solvent. The TBN was 1052 or 22.7% magnesium by titration. The analysis by atomic absorption was as follows:

| | | |
|---|---|---|
| Mg | 25% | |
| K | 40 | ppm |
| Na | 255 | ppm |
| Ca | 1750 | ppm |
| Na + K/Mg | = 40 + 255/250,000 | = 1/847 |
| Ca/Mg | = 1750/250,000 | = 1/143 |

We claim:

1. In the method of preparing overbased magnesium sulfonates by sulfonating an alkyl benzene with a material containing $SO_3$, which material is selected from one member of the group consisting of $SO_3$ and oleum and reacting the alkyl sulfonate product with magnesium oxide in the presence of a low viscosity diluent, water, alcohol, and $CO_2$; which comprises positively utilizing oleum in the sulfonation step and additionally adding to the magnesium oxide a surfactant couple comprising a $C_{12}-C_{18}$ fatty acid and an alkanol amide.

2. The method of claim 1 wherein an alkyl benzene sulfonic acid with added sulfuric acid is utilized instead of the alkyl benzene sulfonic acid.

3. The method according to claim 1 which consists of using as the surfactant couple oleic acid and lauryl diethanol amide.

4. The method according to claim 1 wherein the magnesium sulfonate product is not filtered.

5. A method of preparing a concentrated over-based magnesium sulfonate which consists of producing a magnesium sulfonate according to claim 1 wherein additionally water and methanol are distilled off and a light low boiling diluent oil is added to produce a slurry.

6. The method according to claim 5 wherein additionally magnesium oxide is added to the slurry.

7. The method according to claim 5 wherein carbon dioxide is additionally bubbled through the slurry at 30°–80° C. with stirring.

8. The method according to claim 5 wherein the heating step is carried out at about 120° C. to distill off the water and alcohol.

* * * * *